United States Patent [19]

Vogt et al.

[11] Patent Number: 5,116,762
[45] Date of Patent: May 26, 1992

[54] METHOD FOR DETERMINING THE CONCENTRATION OF FRUCTOSAMINE USING A STANDARD SOLUTION AND METHOD OF CALIBRATING THE STANDARD SOLUTION

[75] Inventors: Bernd Vogt, Tutzing; Hans-Dieter Lessmann, Hirschber-Grossachsen; Christian Klein, Weilheim; Wolfgang Treiber, Seeshaupt, all of Fed. Rep. of Germany

[73] Assignee: Boehringer Mannheim GmbH, Mannheim, Fed. Rep. of Germany

[21] Appl. No.: 377,603

[22] Filed: Jul. 10, 1989

[30] Foreign Application Priority Data

Jul. 19, 1988 [DE] Fed. Rep. of Germany ........ 3824562

[51] Int. Cl.$^5$ .................. G01N 33/66; G01N 33/68
[52] U.S. Cl. ............................... 436/15; 426/8; 426/14; 426/87; 426/88; 426/95; 426/904; 530/345; 530/395; 530/402
[58] Field of Search ........................... 436/8-18, 436/63, 67, 87, 88, 95, 111, 164, 34, 903, 904; 530/300, 345, 350, 395, 402

[56] References Cited

U.S. PATENT DOCUMENTS

| | | | |
|---|---|---|---|
| 4,629,692 | 12/1986 | Dean | 436/518 X |
| 4,642,295 | 2/1987 | Baker | 436/14 |
| 4,645,742 | 2/1987 | Baker | 436/14 |
| 4,761,368 | 8/1988 | Cerami | 435/7.9 |

OTHER PUBLICATIONS

Day et al., J. Biol. Chem., vol. 254, No. 3, pp. 595-597, 1979.
Sela et al., Biochem. J., vol. 85, pp. 223-242, 1962.
Yosizawa et al., J. Biochem., vol. 51, No. 4, pp. 233-241, 1962.
Katchalski, Enzymology, vol. III, pp. 540-555, 1957.
Roche Company Leaflet No. 07 28330, "Fructosamine Test Plus", Apr. 1989.
Schleicher, Erwin D. and Bernd W. Vogt, Clin. Chem. 36:No. 1, 1990.
Vogt, B. W., et al. "Recent Progress in Clinical Chemistry".
Lab. Med. 13: 245:253 (1989), J. D. Kruse-Jarres et al.
Hill, R. P., et al. Ann. Clin. Biochem. 27:413-424 (1990).
Rauen and Kuhn, Biochemisches Taschenbuch Springer-Verlag. 1964-pp. 780-781.

Primary Examiner—Robert J. Hill, Jr.
Attorney, Agent, or Firm—Felfe & Lynch

[57] ABSTRACT

The present invention provides a process for the determination of fructosamine in body fluids using as a standard, a solution which contains a peptide or protein, the amino acid units of which consist of at least 25% of lysine and/or ornithine and is present in glycosylated form.

The present invention also provides a standard solution for the determination of fructosamine containing a peptide or protein, the amino acid unit content of which consists of at least 25% lysine and/or ornithine and is present in glycosylated form, and a method of calibrating such a standard solution.

9 Claims, No Drawings

METHOD FOR DETERMINING THE CONCENTRATION OF FRUCTOSAMINE USING A STANDARD SOLUTION AND METHOD OF CALIBRATING THE STANDARD SOLUTION

The present invention is concerned with a process for the determination of fructosamine in body fluids, as well as with a standard solution suitable therefor.

In the case of diabetic metabolic states, proteins are glucosylated by the excess glucose present in the blood. The carbonyl group of the glucose thereby first reacts with free protein amino residues with the formation of Schiff's bases. By Amadori rearrangement, fructosamines are then formed which have a stable ketoamine bond. Because of the stability of this ketoamine bond, the half-life time of the fructosamines is practically identical with that of the serum proteins. Therefore, fructosamines are suitable as a so-called integral diabetes parameter, i.e. they permit a statement regarding the average blood glucose level over recent weeks.

As one indicator, there has hitherto been used glucosyl-haemoglobin, which is designated as $HbA_1$. The monitoring of this parameter can be used for the long-term monitoring of the sugar metabolism. Since, because of its long half-life time, glucosylhaemoglobin only documents comparatively long-term changes of the metabolic state and the slowness of the haemoglobin decomposition has the result that: short-term metabolic variations are not recognizable, this parameter is not sufficient for a medium-term monitoring of the metabolic control.

On the other hand, the sugar metabolism in the case of diabetics is also monitored by the determination of the blood glucose level. Since, however, the blood glucose level is subject to very considerable variations, it only provides the physician with information regarding the metabolic state at the time of taking the blood sample. This gap between short-term monitoring by means of the blood serum level and the long-term control by the determination of $HbA_{1c}$ is now filled by the determination of the glycosylated proteins, which are referred to as fructosamines. Various studies have shown that the determination of serum fructosamine is a dependably specific and practical method for monitoring in the case of diabetics.

Known processes for the determination of fructosamine, such as have been described, for example, by Johnson et al., Clin. Chem. Acta, 127, 87–95/1982, depend upon the fact that fructosamine, which is present in an aqueous alkaline medium in enol form and can easily be oxidized in this form, is oxidized with an oxidising agent which, in the reduced form, is coloured, for example a tetrazolium salt. The formazane coloured material thereby formed can then be measured photometrically and is proportional to the amount of fructosamine. A further process for the determination of fructosamine, which depends upon an HPLC separation, is described in J. Clin. Chem. Clin. Biochem., 19, 81–87/1981.

In order to make possible a precise determination, it is necessary to produce a calibration curve with standard solutions in order then, in the case of carrying out a determination in a sample solution, to ascertain the value obtained by comparison with the calibration curve. Furthermore, for the precision control of the method of determination and for the calibration of automatic analysers, it is necessary to use standard solutions with known content. Standard solutions which are used for this purpose must contain the measurement parameter to be determined in known concentration. The concentration of the parameter must lie in the medically relevant measurement range. The handling of the standard solutions must be simple and, in particular, they must have a storage stability which is as long as possible.

The hitherto known standard solutions for fructosamine determinations do not fulfil some or several of these prerequisites. Thus, on the one hand, control or calibration sera are used which simulate the serum fructosamine concentration in the form of model substances. For this purpose, 1-deoxy-1-morpholinofructose (DMF) is usually employed. Such primary standards are prepared, for example, by weighing definite amounts of DMF into albumin solutions. It is a disadvantage of these known standard solutions that the model substance DMF has a different structure, therefore behaves quite differently and possesses a reactivity different from that of serum fructosamine so that a comparison of values obtained with a calibration curve with DMF provides values which are much too high. Therefore, the results thus obtained are expressed as DMF units.

On the basis of these primary standards, standard solutions which contain serum fructosamine can then be calibrated. However, such (secondary) standards show, after storage for several days at $+35°$ C., a great instability of the serum fructosamine concentration. In the case of the simultaneous presence of glucose, an increase of the fructosamine content of 200% and more is observed, which is attributed to a continuing nonenzymatic protein glucosylation. On the other hand, in the case of an exclusion of glucose, a decrease of the fructosamine value is observed.

Therefore, it is an object of the present invention to provide not only primary but also secondary standard solutions for the determination of serum fructosamine which are simple to handle, the concentration of which is easy to determine and which can be stored for a long period of time without losing their stability.

Thus, according to the present invention, there is provided a process for the determination of fructosamine in body fluids, wherein, for the calibration, as standard solution there is used a solution which contains a peptide or protein, the amino acid units of which consist of at least 25% of lysine and/or ornithine and is present in a 5 to 50% glycosylated form.

By fructosamines in the meaning of the present invention are to be understood non-enzymatically glycosylated serum proteins (glycated serum proteins), for example glycosylated albumin, immunoglobulin or fibrinogen, as well as non-enzymatically glycosylated blood proteins, for example lysine-glycosylated haemoglobin and glycosylated erythrocyte membrane protein.

According to the present invention, a standard solution is provided which contains the parameter serum fructosamine in a form similar to glycosylated serum protein and the serum fructosamine value of which can simply be ascertained by C/N analysis. A further advantage of the standard solution according to the present invention is that it can be used as a completely synthetic matrix which cannot give rise to any danger of infection.

For this purpose, a solution of artificially glycosylated peptides or proteins is prepared and the particularly desired concentration adjusted. By variation of the added amounts, standard solutions can thus be provided for normal and pathological serum fructosamine concentrations. The preparation of the glycosylated peptide or protein can, for example, take place analogously to a process described by J.F. Day et al., J. Biol. Chem. 254 (3), 595–597/1979 in which an aqueous serum albumin solution is thereby incubated with glucose at 25° C. for 8 days and subsequently dialysed for the removal of free glucose.

In the case of the process according to the present invention, as standard solution there is used a solution which consists of a peptide or protein, the amino acid units of which consist of at least 25% lysine and/or ornithine and is present in glycosylated form. The peptide or protein used should contain at least 5 lysine or ornithine units, possibly with further amino acid units. In a preferred embodiment, there is used a polylysine, a polyornithine or a copolymer of lysine and ornithine. Such polyamino acids can be prepared, for example, according to Methods in Enzymology, Volume III, p. 540/1957, pub. Academic Press, New York; and J. Biochem., 85, 233/1962.

A peptide is preferably used, the molecular weight of which is greater than about 1000. The size of the peptide or protein is, in itself, not critical However, the molecule should still be soluble so that proteins with molecular weights of up to about 300,000 and preferably of up to about 150,000 can be used.

The peptide or protein used is 5–50% glycosylated in known manner by incubating the peptide or protein with glucose. The glycosylation of the peptide or protein is preferably carried out until up to 5 to 50%, preferably 5 to 35%, of all amino side groups are glycosylated. The reaction product is subsequently thoroughly dialyzed As peptide or protein, there can be used not only natural ones but also those prepared synthetically. Especially preferably, there is used poly-L-lysine or poly-L-ornithine in glycosylated form, in which case the fructosamine content can be determined by simple C/N elementary analysis.

The peptide or protein is dissolved in an aqueous medium. In addition, human serum can also be used as basis solution.

It is advantageous when the solution is free of glucose since, in this way, a long storage stability can be ensured. Therefore, in the case of the use of human serum, this must be freed from glucose. This can take place, for example, by dialyzing the human serum against a glucose-free buffer.

Furthermore, the standard solution can contain substances which are conventional for calibration sera. Thus, for example, there can be added clarification agents, stabilising agents, detergents and preserving materials. As clarification agent, there can, for example, be used pentaerythritol. As stabilising agents, zinc and ethylenediamine-tetraacetic acid are especially preferred. As preserving agents, there can be used, for example, phenols or antibiotics. Other auxiliary materials known to the expert can also be used.

The standard solution used according to the present invention is prepared by mixing the individual components and possibly adjusting the pH value by the addition of a buffer system.

The standard solution is subsequently usually filtered free of micro-organisms and can then be lyophilized for comparatively long storage.

In an especially preferred embodiment, the standard according to the present invention is stored in acidic solution, preferably at a pH value below 6 and especially preferably at a pH value of from 0 to 4. Surprisingly, the standard is thereby so well stabilised that a lyophilisation is not necessary and the standard can be stored for a long time in solution. The necessary pH value can be achieved by the addition of inorganic or organic acids, for example hydrochloric acid, citric acid or acetic acid, or also by the addition of a buffer.

The standard solution used according to the present invention is extremely stable and provides steep calibration curves so that an exact and sensitive determination of the fructosamine is possible. A comparison of values obtained with the process according to the present invention for the fructosamine concentration with values which have been obtained according to other known processes which are used for the original calibration show that the process according to the present invention is very simple to carry out and agrees well with the original calibration determined by means of $^{14}$C-glucose incorporation.

The present invention also provides a standard solution for the determination of fructosamine in body fluids, wherein it contains a peptide or protein, the amino acid units of which consist of at least 25% lysine and/or ornithine and is present in glycosylated form.

The standard solution provided according to the present invention has the same structure and thus the same reactivity as naturally-occurring fructosamine. Therefore, the standard solution according to the present invention can be used for the original standardisation of secondary standards and control sera, as well as standard solution for the calibration of fructosamine determinations.

The following Examples are given for the purpose of illustrating the present invention:

EXAMPLE 1

Preparation of polylysine fructosamine 500 mg. Poly-L-lysine (producer: Sigma Chemie, Federal Republic of Germany, average M.W. 39,000) and 120 mg. D(+)-glucose were weighed into a 250 ml. round-bottomed flask and suspended in 50 ml. glacial acetic acid. The reaction mixture was stirred for one hour at ambient temperature, a homogeneous suspension thereby being obtained. Thereafter, 50 ml. pyridine were slowly added dropwise, the suspension was stirred for 8 days at ambient temperature and subsequently poured into 300 ml. desalinated water. A clear solution was thereby obtained which was concentrated to 10 ml. It was then made up to about 350 ml. with 300 ml of 0.02% hydrochloric acid and again concentrated to 10 ml. This procedure was repeated six times with 0.02% hydrochloric acid until the odour of pyridine had disappeared. Subsequently, washing was carried out six times with desalinated water until the filtrate was neutral. The product was then lyophilized from a volume of 50 ml. aqueous solution.

The degree of glycosylation of the product obtained was determined by elementary analysis via the C/N ratio. For one lysine unit, the C/N ratio is 3.0 and for one glycosylated lysine unit is 6.0.

In the present case, the degree of glycosylation lies at 30% of all lysine side groups.

EXAMPLE 2

Various calibration solutions in control sera based on human serum were calibrated in a fructosamine test. The reagent had the following composition: 2.2% non-ionic detergent, 4 U/ml. uricase and 0.5 mmol/liter nitrotetrazolium blue (NBT) in 0.2M carbonate buffer (pH 10.30).

In each case, 50 μl. of sample of human serum with differing fructosamine content were mixed in each case with 1000 μl. of reagent and the extinction increase was measured on a photometer between the 10th and 15th minutes at 546 nm and 37° C. against a reagent blank value.

The following solutions were used for the calibration:
a) a polylysine fructosamine solution, the fructosamine content of which had previously been determined by C/N elementary analysis;
b) a polylysine fructosamine solution, the fructosamine content of which had been determined in a scintillation counter after incubation with $^{14}$C-glucose and subsequent thorough dialysis;
c) a human serum albumin solution, the fructosamine content of which had been determined by in vitro glycosylation with $^{14}$C-glucose according to the method of Johnson et al., Clin. Chem., 32, 368-370/ 1986.

The results for these different standard solutions and control sera are summarized in the following Table 1. The results show that glycosylated polylysine has the same reactivity in the colour test as physiologically occurring fructosamine.

TABLE 1

|          | method a | method b | method c |
|----------|----------|----------|----------|
| sample 1 | 268      | 267      | 268      |
| sample 2 | 279      | 269      | 274      |
| sample 3 | 515      | 491      | 512      |
| sample 4 | 524      | 504      | 517      |
| sample 5 | 390      | 387      | 390      |
| sample 6 | 398      | 391      | 395      |

EXAMPLE 3

The stability of standard solutions according to the present invention was investigated after the addition of acids in various concentrations. For this purpose, solutions of polylysine fructosamine prepared according to Example 1 were dissolved in the appropriate acid. A test series of undiluted solutions were stored for 3 weeks at −18° C. and a further test series each stored for 3 weeks at 35° C. Subsequently, the fructosamine finding again was determined. The results obtained are given in the following Table 2. It can be seen that, after storage for 3 weeks with temperature stressing, the detectable fructosamine content is practically unchanged.

TABLE 2

| acid | fructosamine finding again after | |
|------|----------------------------------|---|
|      | 3 weeks at −18° C. | 3 weeks at 35° C. |
| 0.01 mol/l. hydrochloric acid | 102.3% | 101.1% |
| 0.1 mol/l. hydrochloric acid | 100.4% | 100.1% |
| 0.01 mol/l. acetic acid | 100.6% | 98.0% |
| 0.1 mol/l. acetic acid | 100.4% | 97.9% |
| 0.1 mol/l. citric acid | 99.1% | 97.1% |

TABLE 2-continued

| acid | fructosamine finding again after | |
|------|----------------------------------|---|
|      | 3 weeks at −18° C. | 3 weeks at 35° C. |
| 0.01 mol/l. citric acid | 99.9% | 96.6% |
| 0.001 mol/l. citric acid | 99.8% | 94.9% |

EXAMPLE 4

Preparation of poly-L-lysine-L-phenylalanine fructosamine

Poly-L-lysine-L-phenylalanine (firm Sigma Chemie, average M.W. 46,000) is reacted with glucose analogously to Example 1. With the help of elementary analysis, from the C/N ratio there is obtained a degree of glycosylation of 38.5%.

EXAMPLE 5

Preparation of poly-L-ornithine fructosamine

Poly-L-ornithine (firm Sigma Chemie, average M.W. 32,000) is reacted with glucose analogously to Example 1.

EXAMPLE 6

Preparation of poly-L-ornithine-L-leucine fructosamine.

Poly-L-ornithine-L-leucine 1:1 (firm Sigma Chemie, average M.W. 35,000) is reacted with glucose analogously to Example 1.

EXAMPLE 7

Preparation of poly-L-lysine fructosamine with differing degrees of loading

Poly-L-lysine (firm Sigma Chemie, average M.W. 39,000) is reacted with glucose analogously to Example 1.

In the case of a reaction time of 15 hours at ambient temperature, there is obtained a product which, according to the C/N ratio from the elementary analysis, is glycosylated to an extent of 5.1%.

In the case of a reaction time of 64 hours at ambient temperature, there is obtained a product which, according to the C/N ratio from the elementary analysis, is glycosylated to an extent of 8.1%.

In the case of a reaction time of 120 hours at ambient temperature, there is obtained a product which, according to the C/N ratio of the elementary analysis, is glycosylated to an extent of 14.8%.

EXAMPLE 8

Preparation of poly-L-lysine fructosamine of low molecular weight

Poly-L-lysine (firm Sigma Chemie, average M.W. 3300) is reacted with glucose analogously to Example 1. According to the C/N ratio of the elementary analysis, the product is glycosylated to an extent of 49%.

EXAMPLE 9

Preparation of poly-L-lysine fructosamine of higher molecular weight.

Poly-L-lysine (firm Sigma Chemie, average M.W. 102,000) is reacted with glucose analogously to Example 1. According to the C/N ratio of the elementary analysis, the product is glycosylated to an extent of 28%.

It will be understood that the specification and examples are illustrative but not limitative of the present invention and that other embodiments within the spirit and scope of the invention will suggest themselves to those skilled in the art.

We claim:

1. A method for the determination of the concentration of fructosamine in a body fluid sample comprising
    measuring a characteristic of the body fluid related to fructosamine, and
    using a glucose-free peptide or protein-containing solution having a pH value range of less than 1 to 4 as a standard solution for calibration wherein the peptide or protein contains amino acid units comprising at least 25% of lysine, ornithine or mixtures thereof and the protein or peptide is glycosylated and wherein the characteristic of the body fluid sample solution is compared to the standard solution to determine the fructosamine concentration of the body fluid.

2. The method of claim 1, comprising using polylysine, polyornithine or a co-polymer of lysine and ornithine as the peptide or protein.

3. The method of claims 1 or 2 comprising using a peptide or protein-containing solution wherein the peptide or protein has a molecular weight of 1000 to 300,000 daltons.

4. The method of claim 3 comprising using a peptide or protein of 1000-150,000 daltons molecular weight.

5. The method of claim 1 or 2 comprising using human serum as a base solution for the standard solution.

6. The method of claim 1 comprising using a peptide- or protein wherein 5 to 50% of all amino side groups of the peptide or protein are glycosylated.

7. The method of claim 6, comprising using a peptide or protein wherein 5 to 35% of all amino side groups of the peptide or protein are glycosylated.

8. The method of claim 1 comprising using a standard solution having a buffer system.

9. A method for the calibration of a standard for the determination of fructosamine in body fluids comprising
    analyzing a series of known concentrations of a standard solution by a test for fructosamine in order to compare those results to a similar test result for a body fluid wherein the body fluid test result is compared to that of the standard in order to determine the fructosamine content of the body fluid and
    wherein the standard solution has a pH value of less than 1 to 4 and is a glycosylated peptide or protein with an amino acid content comprising at lest 25% of lysine, ornithine or mixtures thereof.

* * * * *